United States Patent [19]

Palmer et al.

[11] 4,201,477
[45] May 6, 1980

[54] SUSPENDED SOLIDS METER

[75] Inventors: Warren G. Palmer, Saratoga; John N. Pritchard, San Jose, both of Calif.

[73] Assignee: FMC Corporation, San Jose, Calif.

[21] Appl. No.: 869,882

[22] Filed: Jan. 16, 1978

[51] Int. Cl.² .......................................... Q01N 21/24
[52] U.S. Cl. .................................... 356/434; 356/442
[58] Field of Search ............... 356/205, 208, 246, 433, 356/434, 436, 440, 441, 442; 350/63

[56] References Cited

U.S. PATENT DOCUMENTS

| | | | |
|---|---|---|---|
| 3,518,439 | 6/1970 | Furmann | 356/208 |
| 3,751,340 | 8/1973 | Witz | 356/208 |
| 3,873,273 | 3/1975 | Moran et al. | 356/246 |
| 3,903,877 | 9/1975 | Terada | 350/63 |
| 4,027,981 | 6/1977 | Steinbatz | 356/205 |

OTHER PUBLICATIONS

U.S. Environmental Protection Agency pamphlet EPA-670/2-75-002, Apr. 1975 "Suspended Solids Monitor".
Suggested Specification Sheet, Biospheric Inc. Model 52LE Suspended Solids Meter, dated Mar. 1, 1976.
Specification and pamphlet for the Sonic Solution monitor, Nusonics, Inc. Printed Mar. 1974.

*Primary Examiner*—John K. Corbin
*Assistant Examiner*—R. A. Rosenberger
*Attorney, Agent, or Firm*—R. S. Kelly; H. M. Stanley; F. W. Anderson

[57] ABSTRACT

An optical sensing head is provided for immersion in a solution carrying suspended solids and includes a chamber exposed to the solution and defining a sample path which extends through the solution. A spray mechanism is provided which forcefully removes light attenuating deposits which may accumulate on the surfaces of the chamber structure forming the sample path. A light beam is directed along an optical path (which includes as a portion thereof the sample path), and a light sensor is disposed at the other end of the optical path providing a signal indicative of the intensity of the received light. Plumbing is provided through which the exposed chamber may be flooded with clear water to thereby provide a low level suspended solids concentration for use as a reference. A light absorbing member is provided which is selectively positioned across the optical path to provide a high level suspended solids concentration reference when so positioned. A controller receives the light sensor signal and operates to control the spray mechanism, the flooding function, and the positioning of the light absorbing member in a predetermined sequence. The sensing head and its control system provide a suspended solids measurement with a predetermined scale factor over a predetermined range and further provide a correction when the optical path or controller circuit characteristics change. When the control is unable to properly provide the correction, an error indication is provided so that the suspended solids concentration readings will be known to be inaccurate.

19 Claims, 8 Drawing Figures

FIG_1

FIG_2

FIG_3

FIG 5

FIG_6

FIG_7

FIG_8

SUSPENDED SOLIDS METER

BACKGROUND OF THE INVENTION

1. Field of the Invention

This invention relates to a meter for measuring the suspended solids content in a liquid, and more particularly, to such meters for use in monitoring suspended solids content of a liquid which utilize sensing means for determining the transmission characteristics of a light beam passed through the liquid.

2. Description of the Prior Art

It is well established that a measurement of the concentration of solids suspended in a solution may be made by measuring the attenuation and/or scattering of a visible or near infrared light beam directed along a path extending through the solution. Optical windows are aligned with the path along which the light beam is directed. The major problem with this method of measurement is associated with keeping the optical windows free of light absorbing coatings deposited by the solution being monitored. Further, there is usually no way of knowing when the measurement system is providing satisfactory measurements or is producing erroneous indications due to meter malfunctions rather than change in the suspension conditions within the solution.

Several instruments are presently available which perform the functions of detecting and providing an indication of the quantity of particulate material suspended as solids in a solution. Schemes utilizing the effect of the suspended solids on the transmission of a light beam are the most common. The United States Environmental Protection Agency pamphlet, entitled Suspended Solids Monitor, by John W. Liskowitz and Gerald J. Franey, EPA-670/2-75-002, dated April 1975, discloses a device in which polarized light is directed into a solution containing suspended solids. The polarized light is scattered by the solids in suspension, and the amount of scattering is detected and processed to provide an indication of the suspended solids concentration. This scheme is more suitable for detection of a low concentration of suspended solids in solution and might more accurately be termed a turbidity meter.

Other forms of suspended solids detection apparatus are available using the light transmission principle, one of which includes a mechanical wiping structure for cleaning the optical windows along the light beam path through the solution. Such a device is manufactured by Biospherics Inc. of Rockville, Maryland as suspended solids meter Model 52LE. However, the accuracy of operation of such a device cannot be checked without removing the device from the site of operation and returning it to a laboratory for an accuracy test. As a consequence, the efficiency of the window cleaning function is unknown, and erroneous readings may be obtained if window cleaning is incomplete. No indication of the error is provided to those who utilize the obtained data.

A measurement of suspended solids in solution has also been made ultrasonically. A device utilizing such a system is manufactured by Nusonics, Inc. of Paramus, New Jersey and sold as a Sonic Solution Monitor. Such device comprises a transducer head and a receiver head which are immersed in a solution being monitored. The attenuation of the sound energy passed through the solution is measured to obtain an indication of the concentration of solids suspended in the solution. The ultrasonic method is subject to providing erroneous data without error indication if the solids in suspension change from one material to another or if changes occur in the associated electronic circuitry.

It is apparent that a suspended solids meter which retains its preset laboratory calibration characteristics throughout a prolonged period of usage, which provides an error indication when output data is unreliable, and which automatically recalibrates to assure continuous accuracy of data will be highly desirable to users of such devices.

SUMMARY OF THE INVENTION

In general, the disclosed structure for detecting the concentration of solids suspended in a solution includes a sensor head which is adapted to be immersed in the solution being monitored. The sensor head has a chamber disposed for communication with the monitored solution. Structure is provided which defines an optical sample path of a predetermined length through the chamber. A light source is located in the sensor head which directs light energy along the sample path. A light sensor is also located in the sensor head being positioned to intercept the light energy which has traversed the predetermined length of the sample path. The light sensor provides an output related to the intensity of the light energy received. Means is provided which periodically directs a flooding solution to the chamber to flood the predetermined path length with a solution which is substantially free of suspended solids. While the sample path length is flooded, a low concentration reference for suspended solids is provided. In this fashion periodic light sensor outputs are obtained which define the low end of a predetermined suspended solids concentration range within which measurements are to be taken. A light absorbing member is provided which is movable between a position lying across the sample path and an out of the way position. When across the path a predetermined portion of the light energy is absorbed and a point toward the high end of the suspended solids concentration range is defined. Means is provided to alternately fill the path with flooding solution and to insert the absorbing member across the path so that the light sensor output may be calibrated to provide correction for subsequent suspended solids readings.

The method disclosed for measuring the concentration of solids suspended in a solution within a predetermined concentration range includes the steps of defining a measurement path of predetermined length within the solution and directing a light beam therealong. Sensing the intensity of the light beam after it has traversed the measurement path provides an output signal indicative of the amount of light which has been scattered or absorbed by solids suspended in the path and is therefore indicative of the concentration of suspended solids in the measurement path. The measurement path is periodically flooded with a solution substantially free of suspended solids, and the output signal obtained during the flooding is stored as a low level suspended solids concentration reference. A predetermined portion of the light is periodically absorbed along the measurement path and the output signal obtained is stored as a high level suspended solids concentration reference. Adjustment is then made to subsequent suspended solids readings in accordance with the low concentration reference measurement so that the subsequent readings are in conformance with the scale defined by the predetermined concentration range.

It is an object of the present invention to provide a suspended solids concentration metering apparatus which periodically performs a self-cleaning function.

It is another object of the present invention to provide a suspended solids concentration metering apparatus which automatically performs a self-calibration function.

It is another object of the present invention to provide a suspended solids concentration metering apparatus and method which automatically provides an error indication when the meter is fouled and readings are unreliable or invalid.

Additional objects and features of the invention will be apparent from the following description in which the preferred embodiment has been set forth in detail in conjunction with the drawings.

DESCRIPTION OF THE PREFERRED EMBODIMENTS

Figure 1:
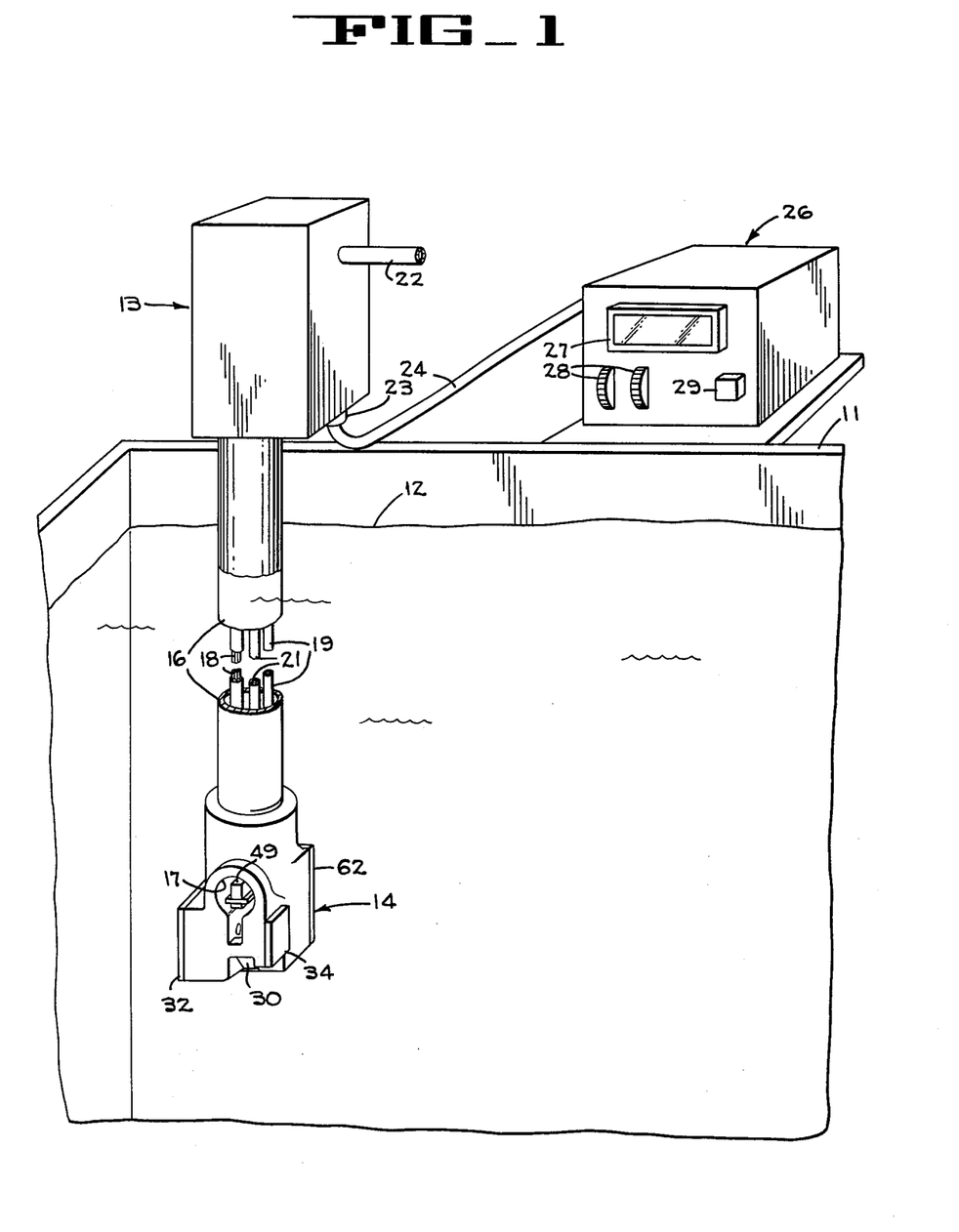
FIG. 1 is an isometric view of the suspended solids concentration meter of the present invention illustrating its use in metering a solution in a tank.

A holding tank 11 is shown in FIG. 1 containing a solution 12 which has suspended therein a concentration of particulate solids. The suspended solids concentration measurement apparatus disclosed herein is shown as including a control valve console 13 and a sensor head 14 with an elongate tubular interconnect housing 16 extending therebetween. Sensor head 14 has an external chamber 17 comprising a recess (see FIG. 3) formed in one wall thereof which is in communication with the solution 12. Tubular interconnect housing 16 is connected to sensor head 14 in sealed fashion and carries an electrical cable 18 and a pair of tubes 19 and 21 adapted to provide fluid to the head. The housing 16 is connected to a control valve console 13 which has a water inlet pipe 22 connected to the tubes 19 and 21 and connected externally of the console to a supply of clean water or some other suitable solution substantially devoid of suspended solids. By means to be pointed out in greater detail hereinafter, the control valve console controls the flow through the tubes 19 and 21 to the sensor head. An electrical connector 23 is also provided on control valve console 13 to receive an electrical cable 24 extending between the control valve console 13 and a meter control console 26, said cable 24 providing a connection to the sensor head cable 18. A bezel 27 is located on the front face of meter control console 26 housing a measurement instrument display. A pair of hexadecimal thumb wheel switches 28 and an on-off power select button 29 are accessible at the front panel of meter control console 26.

Figure 2:
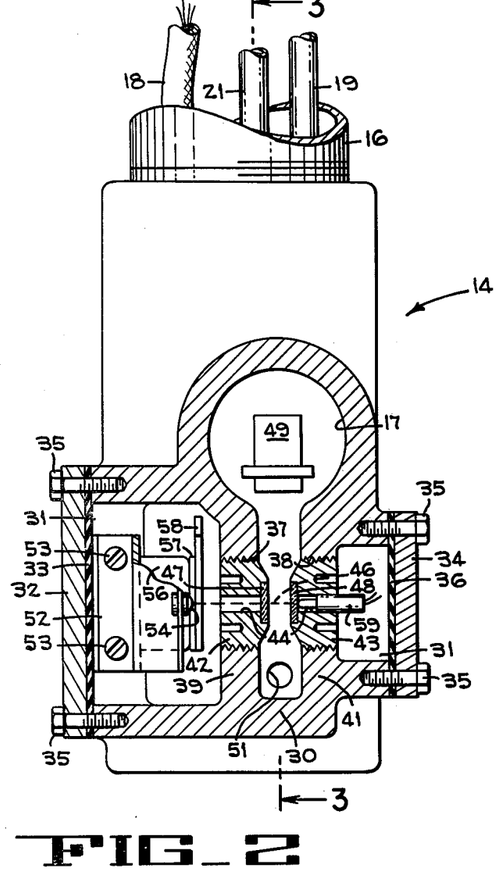
FIG. 2 is an enlarged vertical section through the sensor head of the suspended solids concentration meter.
Figure 3:
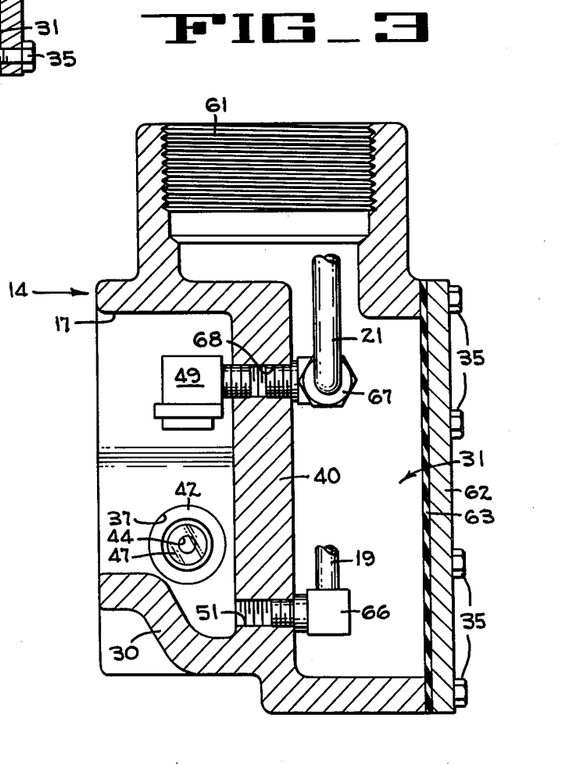
FIG. 3 is a section taken along line 3—3 of FIG. 2 with the interconnect housing being removed.

The sensor head 14 is shown in greater detail in FIGS. 2 and 3. Sensor head 14 has an internal generally U-shaped chamber 31 which is enclosed and sealed by a side cover 32 and associated gasket 33 (FIG. 2), a side cover 34 and associated gasket 36, and a rear cover 62 and associated gasket 63 (FIG. 3). The side covers 32 and 34 and rear cover 62 together with their respective gaskets 33, 36 and 63 are fastened to the main housing of sensor head 14 by means of bolts 35. The wall of the sensor head encloses the front sections of the chamber 31 (FIG. 1). As shown in FIG. 2, the external chamber 17, which is exposed to the surrounding medium, lies within the confines of U-shaped chamber 31 and is separated therefrom by side walls 39 and 41 and a rear wall 40 (FIG. 3). Threaded apertures 37 and 38 (FIG. 2) are formed in the side walls 39 and 41 respectively between the exposed chamber 17 and the enclosed chamber 31. Threaded inserts 42 and 43 are formed to fit in the threaded apertures 37 and 38 respectively, and passages 44 extend through the threaded inserts, the aligned axes of such passages defining a sample path 46 which extends across the chamber 17. A transparent window 47 is mounted in sealed fashion in threaded insert 42 extending across the passage 44. Another transparent window 48 is sealably mounted in threaded insert 43 also extending across the associated passage 44. The predetermined length of the sample path 46 is therefore defined within chamber 17 between the opposing faces of the transparent windows 47 and 48. The threads in the threaded apertures 37 and 38 and on the threaded inserts 42 and 43 may be pipe threads to provide a tight seal between enclosed chamber 31 and exposed chamber 17.

A spray nozzle 49 is shown in FIGS. 2 and 3 disposed in the upper, enlarged portion of external chamber 17 and extending into the chamber. The nozzle is oriented so as to direct a wash spray downwardly toward windows 47 and 48. The force of the spray from spray nozzle 49 is calculated to remove any light absorbing foreign matter which may adhere to windows 47 or 48. A threaded aperture 51 is shown entering chamber 17 near the bottom thereof (FIG. 3) so that a flooding solution may be introduced with minimal turbulence into chamber 17 to substantially fill the predetermined length of sample path 46 extending between the faces of transparent windows 47 and 48.

A bracket 52 is shown in FIG. 2 mounted within enclosed chamber 31 by screws 53. A light source 54 is mounted in bracket 52 in line with sample path 46 so that when energized it directs a beam of light along an optical path (shown in dashed lines in FIG. 2) which is coincident with sample path 46. Light source 54 may be a miniature incandescent lamp or similar type of light source. Bracket 52 also serves as a mount for a rotary solenoid 56 having a rotating plate 57 actuated thereby. An absorbing member 58 is mounted on rotary plate 57, thereby being disposed for motion between a position intercepting the light beam from source 54 and a position remote therefrom. In this embodiment the absorbing member 58 is a neutral density filter which attenuates all of the light energy wavelengths to substantially the same degree. An appropriate absorbing member 58, for example, may be one which attenuates light by a factor of about 640. A light sensing device (or photosensor), such as a phototransistor 59, is mounted adjacent transparent window 48 within the passage 44 in threaded insert 43. Photosensor 59 is positioned to receive the light traversing the sample path 46 and to provide an output signal indicative of the intensity of the received light. Rotary solenoid 56, light source 54, and photosensor 59 are connected to conductors running through cable 18.

As shown in FIG. 3 sensor head 14 has an upper threaded aperture 61 in communication with the enclosed chamber 31 and formed to receive the threaded lower end of tubular interconnect housing 16. The threads in aperture 61 and on the end of interconnect housing 16 are pipe threads in this embodiment to provide a tight seal at the junction between housing 16 and sensor head 14. The tube 19 from the interconnect housing enters an elbow 66 which is threaded into one end of the aperture 51, maintaining the seal between exposed chamber 17 and chamber 31 which is enclosed within the body of the sensor head. Aperture 51 enters into the lower portion of chamber 17 so that fluid, flowing with relatively low turbulence therethrough, will be deflected upwardly by the curved lower wall 30 of chamber 17 to fill the predetermined length of sample path 46 (FIG. 2) extending between the opposing faces of transparent windows 47 and 48.

The tube 21 from interconnect housing 16 enters an elbow 67 (FIG. 3) which is threadably engaged in a threaded hole 68 through the wall 40 between the chamber 17 and the chamber 31 at the upper end of chamber 17. Spray nozzle 49 is threadably engaged in the outlet end of threaded hole 68 so that fluid delivered through tube 21 is emitted forceably from spray nozzle 49 in a downward direction.

Figure 4:
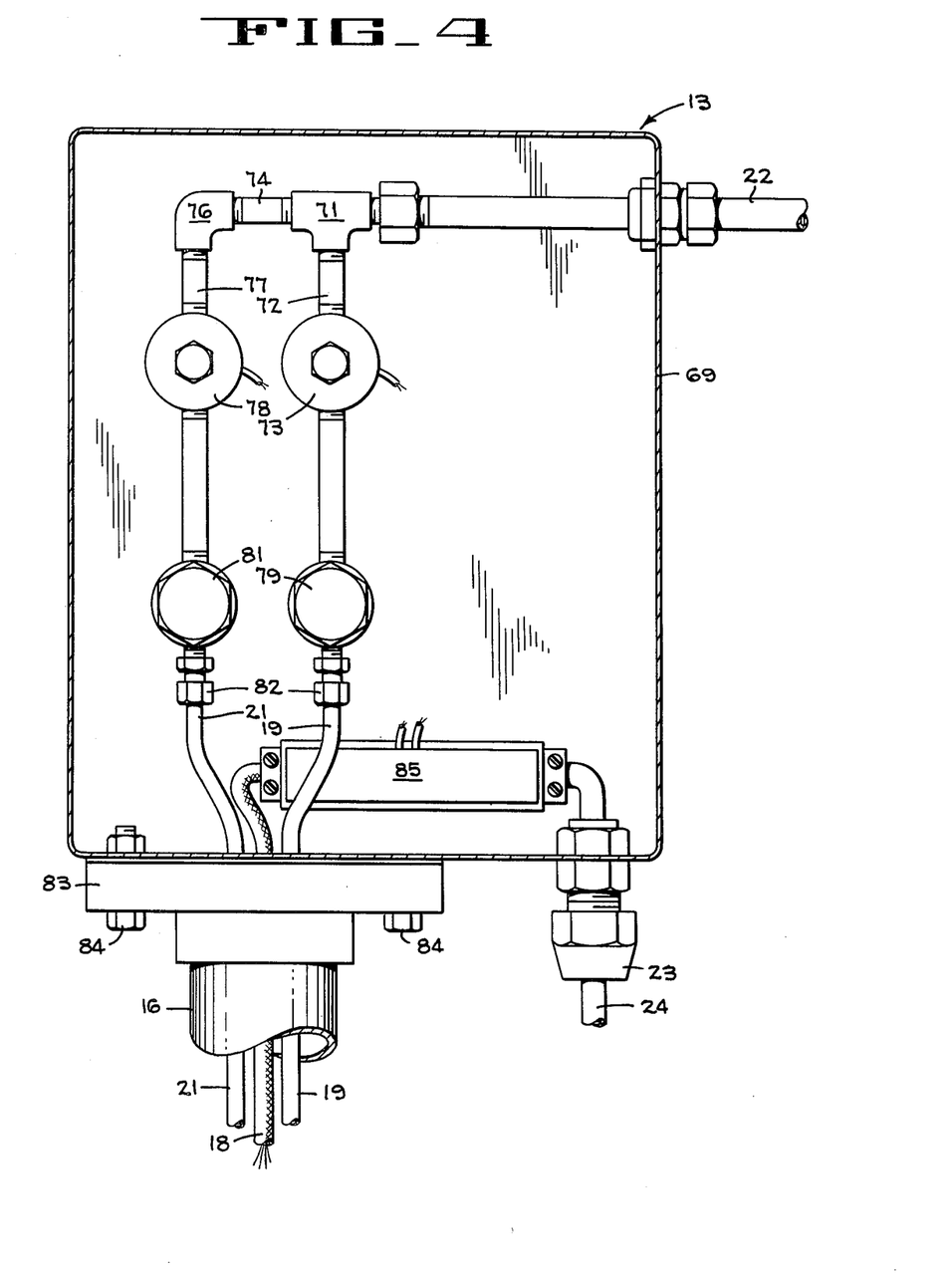
FIG. 4 is an enlarged vertical section through the interior of the control valve console of the suspended solids concentration meter.

Referring to FIG. 4 of the drawings, the control valve console 13 will be described. Water inlet pipe 22 is seen extending through the wall 69 of the control valve console to a "T" fitting 71 which is fastened thereto. Tubing 72 is connected to one outlet of the "T" fitting 71 and leads to a "flooding" solenoid valve 73. Tubing 74 is connected to the remaining open end of the "T" fitting 71 and is joined by an elbow 76 and another length of tubing 77 to a "wash" solenoid valve 78. A flow regulator 79 is coupled to the outlet from flooding solenoid valve 73, and another flow regulator 81 is coupled to the outlet of wash solenoid valve 78. Flow regulators 79 and 81 are connected to tubes 19 and 21, respectively, through appropriate fittings 82 and serve to control the flow of fluid therethrough. In general, flow regulator 79 provides a relatively low flow for flooding aperture 51, and flow regulator 81 provides a relatively high flow for spray nozzle 49. Thus, a scrubbing effect is obtained from the spray from nozzle 49, and a low turbulence flooding effect is obtained from the flow through aperture 51. Water, or some other appropriate fluid devoid of suspended solids, is directed from a source of such fluid through inlet pipe 22, flooding solenoid valve 73 and tubing 19 to 51 in sensor head 14 when solenoid valve 73 is actuated and at a rate determined by flow regulator 79. In like fashion, when wash solenoid valve 78 is actuated to the open position, water is directed from the source, at a rate determined by flow regulator 81, through tubing 21 to spray nozzle 49 in sensor head 14. Electrical power for actuating solenoid valves 73 and 78 between their open and closed positions is provided through power cable 24 and a terminal strip 85. The terminal strip 85 is enclosed within the control valve console to provide terminals for the electrical conductors extending from cable 24, the solenoid valves 73 and 78, and the conductors contained in cable 18 leading to rotary solenoid 56, light source 54, and light sensor 59 in sensor head 14. Tubular interconnect housing 16 passes through the bottom wall of the control valve console and is held in place by means of a clamping plate 83 fastened by bolts 84.

Figure 5:
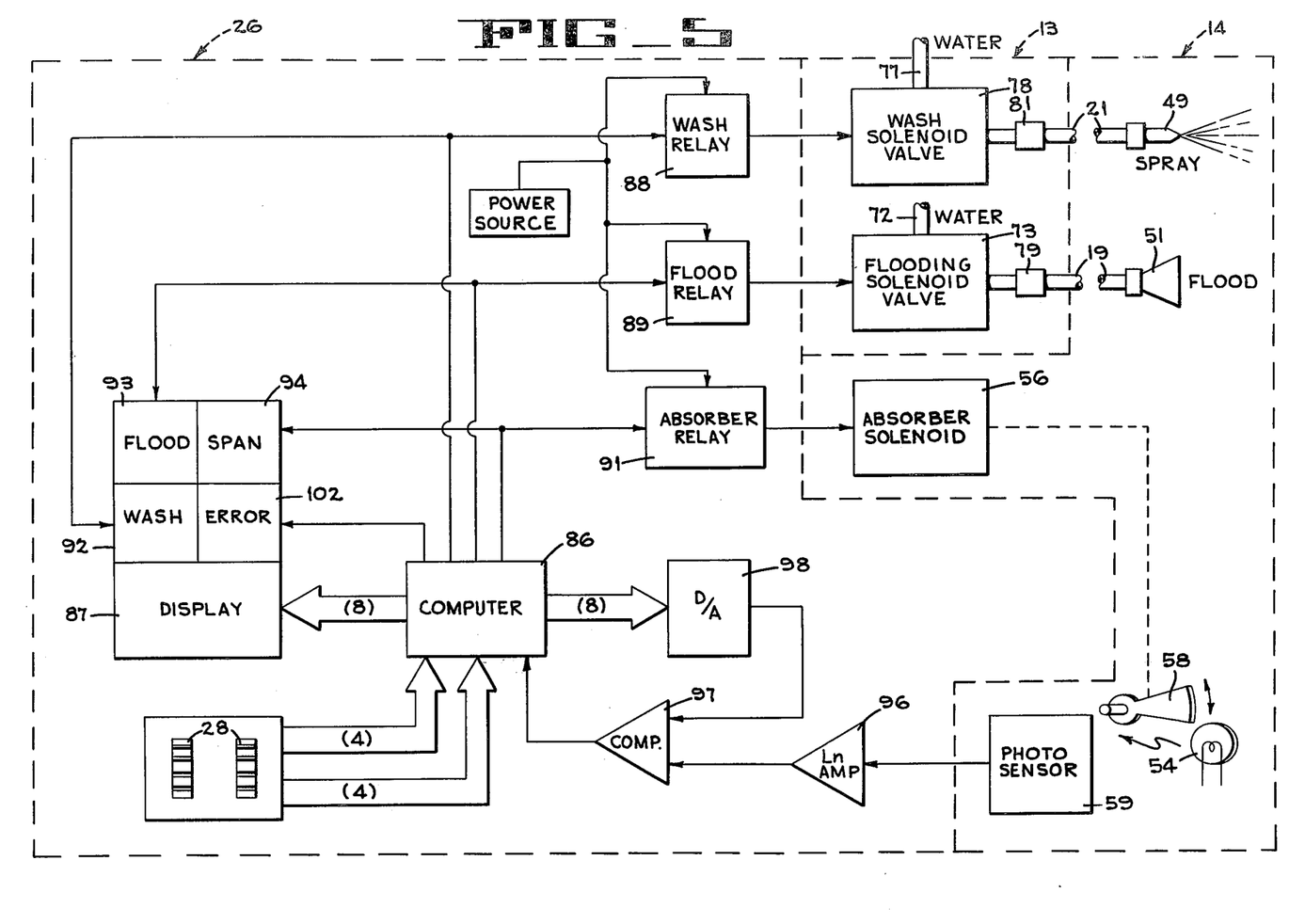
FIG. 5 is a block diagram of the hydraulic and electrical circuitry of the suspended solids concentration meter.

The block diagram of FIG. 5 shows schematically the interconnection between the components in control valve console 13, sensor head 14, and meter control console 26. A computer 86 is provided in meter control console 26, which in this embodiment is a microprocessor that may be of the type currently commercially available as an F8 microprocessor manufactured by Fairchild Camera and Instrument Corporation, Mountain View, California. Microprocessor 86 has two 4-bit input ports coupled to the hexadecimal thumb wheel switches 28, which serve a purpose to be hereinafter described. Microprocessor 86 is programmed to perform a sequence of functions and provides an output to a display 87 which indicates the concentration of suspended solids in parts per million (PPM). Microprocessor 86 also serves to provide output signals to a wash relay 88, a flood relay 89, and an absorber relay 91. Each of relays 88, 89, and 91 is, in the preferred embodiment, a solid state device which provides optical isolation between the input and output terminals. Relays 88, 89, and 91 operate to provide power to the wash solenoid valve 78, the flooding solenoid valve 73, and the absorber rotary solenoid 56 respectively. Wash solenoid valve 78 is thus controlled by microprocessor 86 between an open and a closed position to provide water through flow regulator 81 to spray nozzle 49. In like fashion, flooding solenoid valve 73 is controlled between an open and closed position by microprocessor 86 to thereby deliver water through flow regulator 79 to aperture 51, which serves as a flooding port for the exposed, external chamber 17 of the sensor head.

Actuation of rotary solenoid 56 on the command of microprocessor 86 positions the absorbing member 58 in the optical path between light source 54 and light sensor 59. When the absorbing member 58 is thus positioned to intercept light energy from light source 54, a predetermined portion of the light intensity from light source 54 is absorbed and a high suspended solids concentration in the fluid in sample path 46 is simulated. Thus, a high suspended solids concentration reference is provided for use in calibrating the suspended solids meter. This reference provides an indication of a known high solids concentration value (somewhere between 50–100%, preferably 100%, of the full range or "span" of measurement provided by the meter) and thus determines the accuracy of the meter "span". Recalibration of the meter scale resulting in the shifting of the high concentration reference level may be made necessary by changes in characteristics of various components in the suspended solids meter circuitry. Recalibration of the "zero" end of the scale is provided by the flooding of the sample path 46 and may be made necessary by changes in the characteristics of the optical path (e.g., discoloration or adherence of a film to the windows 47 and 48) as well as circuit component changes which may occur as such components age. Thus, the system of the present invention functions to impose corrections on the suspended solids concentration measurements by sensing the light transmitted over sample path 46 at a known low concentration reference level and a known high concentration reference level. The correction capability of the system for overcoming the reduced transmission of light due to factors other than the nature of the solids concentration of the solution in which the sensor head 14 is immersed and/or the drifting of internal component values has a finite range, and when this range is exceeded the system operates to indicate that an error exists and that the data provided by the system is unreliable. The signals which serve to actuate relays 88 and 89 also serve to illuminate respective wash and flood displays 92 and 93 which indicate that these specific functions are in progress. The signal that actuates the rotary solenoid 56 that moves the absorbing member 58 into the sample path illuminates a "span" display that indicates that the circuitry is checking the accuracy of the upper end of the meter scale.

When a concentration of suspended solids in solution 12 occupies the predetermined length of sample path 46 between the faces of windows 47 and 48, some of the light energy from light source 54 is absorbed by the particles and some of the light energy is scattered thereby. Consequently, the intensity of the light falling on photosensor 59 is reduced. The signal provided by photosensor 59 is therefore also reduced, and the relationship between the transmitted light and the concentration of solids in a liquid through which the light passes is known to be an exponential one by Beers law. The signal from photosensor 59 is connected to the input of a logarithmic amplifier 96 which provides an output signal which is the logarithm of the input. The purpose of the logarithmic amplifier 96 is to linearize the signal coupled to the microprocessor 86 relative to the solids concentration in the sample path. The manner in which this is done may be seen from the following:

Let:
I = light intensity received at photosensor 59.
i = signal current from photosensor 59.

The relationship describing the intensity of light which passes through a solution of suspended solids in terms of the original light intensity produced by a light source is known to be:

$$I = I_o e^{-ACY}$$

Where:
$I_o$ = original light intensity.
A = attenuation coefficient for the suspension, assumed constant.
C = concentration of suspension mg/cm$^3$.
Y = path length between windows 47 and 48 in cm.

The relationship $i = K_1 I = K_1 I_o e^{-ACY}$ is a statement of Beer's law, where i is the signal current from light sensor 59 coupled to the input of logarithmic amplifier 96, and $K_1$ is the photosensor transducer coefficient.

The logarithmic amplifier 96 has the following known relationship:

$$V_o = -K_2 \ln \frac{i}{i_R} = -K_2 \ln \frac{K_1 I_o e^{-ACY}}{i_R}$$

Where:
$V_o$ = amplifier output.
$i_R$ = reference current for logarithmic amplifier.
$K_2$ = amplification factor.
$V_o = K_2 [\ln K_1 + \ln I_o - \ln i_R - ACY]$.

$V_o = K_A = K_B C$.
Where:
$K_A = -K_2(\ln K_1 + \ln I_o - \ln i_R)$ and $K_B = K_2 AY$.
Therefore, the output signal Vo from logarithmic amplifier 96 is a linear function of the concentration, C, of suspended solids in solution 12 since $K_B$ and $K_A$ will be constants.

The logarithmic amplifier 96 is such, in this embodiment, that the output from the logarithmic amplifier is inverted, i.e., it increases as the intensity of the light impinging upon photosensor 59 decreases. Thus, a higher level signal is provided by logarithmic amplifier 96 for higher suspended solids concentrations in solution 12. The output of logarithmic amplifier 96 is coupled to one input of a comparator 97. Microprocessor 86 receives the output signal from comparator 97. The microprocessor provides an 8-bit binary count output to a digital to analog (D/A) converter 98 such that at the start of a measurement sequence (to be described in greater detail hereinafter) the microprocessor begins a counting sequence and sequentially provides the 8-bit digital count outputs to the D/A converter. The 8-digital count output has a finite maximum number (256) although only a portion (200) of the counting range is used in the counting sequence. Each increased count from microprocessor 86 to D/A converter 98 increments the analog output signal from D/A converter 98 so that the output therefrom increases in a stepwise fashion. The increasing output from D/A converter 98 is connected to the other input of comparator 97. For a given signal from the amplifier 96 indicative of suspended solids concentration, the output of comparator 97 will be in one of two possible states. The output from comparator 97 begins at a high state as microprocessor 86 begins to run through the predetermined digital count (0 to 200) to D/A converter 98. As the output from D/A converter 98 increases in step-wise fashion, it should ultimately just exceed the output from logarithmic amplifier 96, and the output from comparator 97 will then assume a low state. This change in output state of comparator 97 is sensed by the microprocessor to indicate a match of the amplifier signal indicative of suspended solids concentration, and the digital count from microprocessor 86 directed to the D/A converter 98 will be arrested. This output count can later be converted by the microprocessor and displayed in display 87 to give an indication to the operator of the solids concentration in the solution in which the sensor head 14 is immersed.

Figure 6:
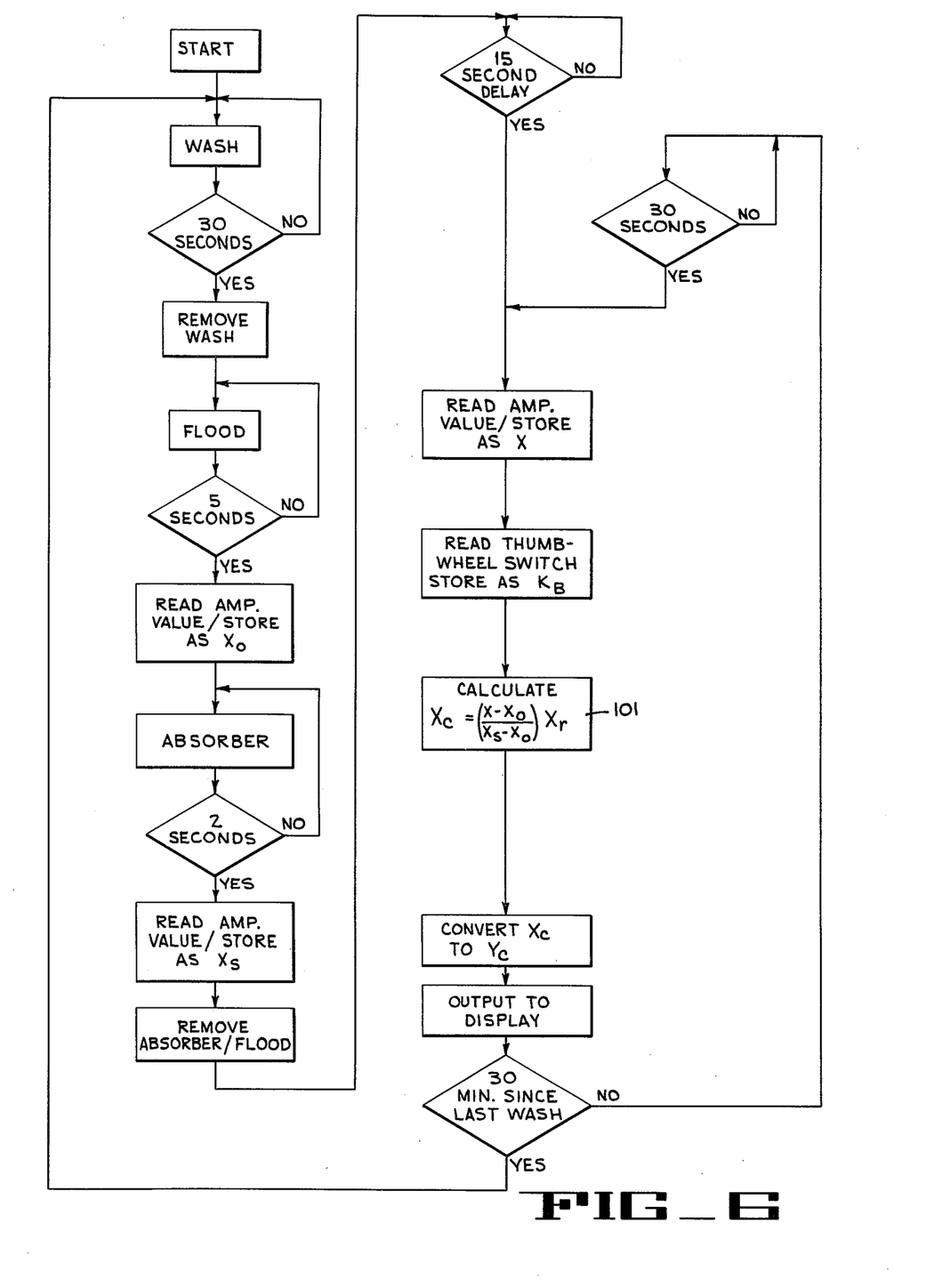
FIG. 6 is a flow chart graphically depicting the manner in which the processing control circuitry of the suspended solids concentration meter is programmed.

Turning to the flow chart of FIG. 6, the manner in which microprocessor 86 is programmed to control the operation of the suspended solids meter is there shown. It will be understood that one skilled in the art can readily program microprocessor 86 based on the information provided in the disclosed flow chart. Power is turned on by actuating the ON-OFF switch 29 (FIG. 1) on the face of the meter control console 26. Microprocessor 86 initiates a "start" instruction, followed by a wash instruction signal which actuates wash relay 88 and illuminates the wash indicator 92 on the meter control console. Wash solenoid valve 78 is therefore actuated to an open position and water under pressure is emitted from spray nozzle 49 forcing foreign matter off of the faces of windows 47 and 48. The wash instruction continues in effect for a period of time, such as 30 seconds as indicated in the flow chart, after which the wash function is removed and wash relay 88 is deenergized. A flood instruction signal is next provided by microprocessor 86 to flood relay 89 and to the flood indicator 93 on the meter control console. Flooding solenoid valve 73 is thus actuated to the open position and a low turbulence flood of water is delivered through aperture 51 in the sensing head to fill the predetermined length of sample path 46. The flooding function is continued for a length of time, such as five seconds (as shown in the flow chart), at the end of which the output of the amplifier 96 is read (in the manner aforedescribed) and stored in microprocessor 86 as $X_o$. Next microprocessor 86 instructs the absorber relay 91 to energize the absorber rotary solenoid 56 and a "span" indicator 94 is illuminated in the display to indicate that the high reference value is being determined. Rotary solenoid 56 positions absorbing member 58 in sample path 46 for a predetermined period of time, such as two seconds as indicated. The amplifier 96 output at the end of the predetermined period of time is read and stored in microprocessor 86 as $X_x$. The actuating signals to flood relay 89 and absorber relay 91 are removed, and flood and span indicators 93 and 94, respectively, are deenergized. Flooding solenoid valve 73 is thus positioned in a closed condition, and rotary solenoid 56 repositions absorbing member 58 in a position remote from sample path 46.

Following a short delay, such as 15 seconds, to allow the flooding solution to emigrate from the sample path 46 and solution 12 to reoccupy the path, microprocessor 86 reads the output signal from the amplifier 96 and stores the value as X. The microprocessor 86 then interrogates the thumbwheel hexadecimal switches 28 which are set to store the constant $K_B$ (see previous equations relative to the amplifier 96 output) that determines the slope of the output curve of the amplifier 96, i.e., the relationship between amplifier output Vo and solids concentration C (see FIG. 8). The setting on thumbwheel switches 28 is stored in the microprocessor 86 as $K_B$ and is used when the microprocessor performs the subsequent calculations to determine the concentration value. The $K_B$ value will not change for any given type of solution 12. However, when a different type of solution, i.e., one having a different type of suspended solids, is to be measured, the value $K_B$ as set by switches 28 may have to be changed. This can only be determined by measuring the new solution with a known suspended solids concentration and adjusting the switches 28 until the proper output is obtained.

Figure 8:
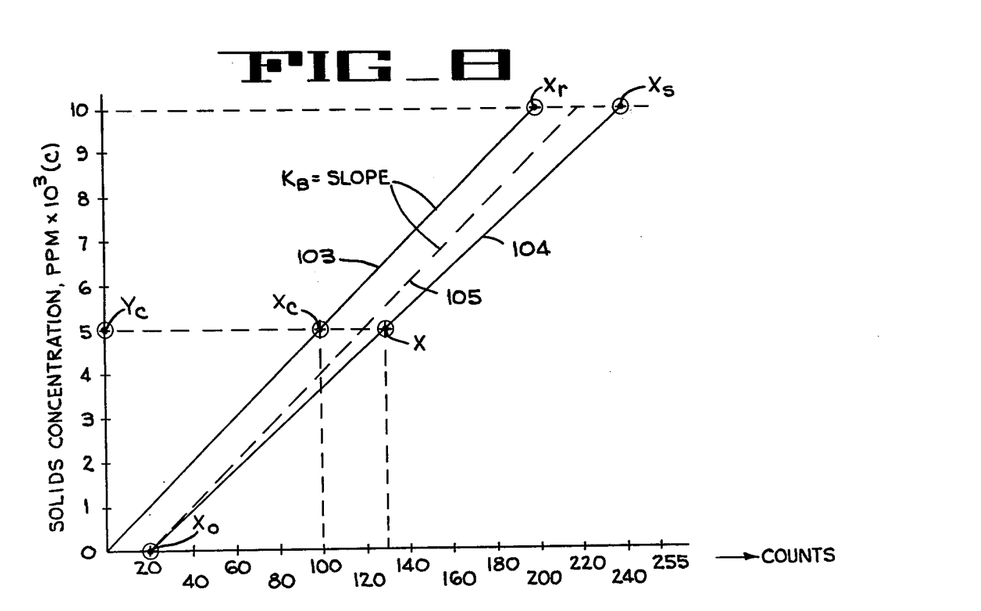
FIG. 8 is a graph describing the manner in which the suspended solids concentration meter is periodically recalibrated.

The microprocessor 86 next performs the calculation indicated in block 101 of FIG. 6 to obtain a corrected voltage output reading, which is indicated as $X_c$. The corrected reading $Y_c$ will correspond to a suspended solids concentration measurement $Y_c$ which will be within a predetermined range from zero concentration to a value wich is shown in FIG. 8 as 10,000 parts per million (PPM). This will also be the high reference value as set by the absorbing member 58 although it will be recognized that a somewhat smaller value than full scale could be used as the reference value if desired. The corrected concentration reading $X_c$ is converted to $Y_c$ which is outputted to display 87 providing a visual indication of the concentration of the suspended solids in parts per million. Microprocessor 86 then interrogates the time since the last wash cycle, and if some suitable time such as 30 minutes has not passed, the solids concentration reading portion of the program is re-entered as indicated. The program will now wait for the remainder of a 30 second time interval since the last reading update in the microprocessor after which a new amplifier output reading is obtained and stored as X in microprocessor 86. The ensuing calculation and output steps are repeated as described until such time (the passage of 30 minutes) as another wash cycle is to be initiated, whereupon the entire program is reinitiated starting with the wash instruction.

Figure 7:
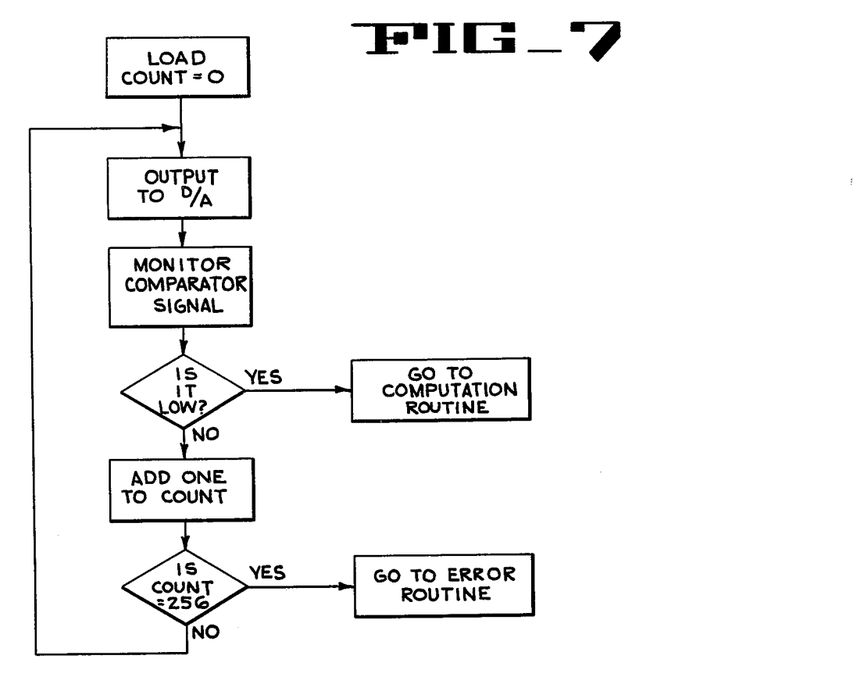
FIG. 7 is a flow chart of a subroutine for use in the basic program depicted in FIG. 6.

The subroutine for those three flow chart boxes indicated in FIG. 6 as "read amplifier value and store" as "$X_o$", "$X_s$" or "X", is shown in FIG. 7. Initially microprocessor 86 starts with a count equal to zero at the ports coupled to the D/A converter 98. Then, the microprocessor 86 output is incremented by one count, resulting in an analog output signal from digital-to-analog converter 98 which is coupled to comparator 97. The microprocessor "looks" at the comparator output making a decision as to whether the comparator output is low. If the comparator output is high, the microprocessor 86 increments by one count the output to D/A converter 98. Microprocessor 86 then makes a decision as to whether or not the count output to the D/A converter 98 is full, i.e., 255 counts. Since this decision is "No", the incremented count is outputted to D/A converter 98, and another comparison is made in comparator 97 between the voltage output from logarithmic amplifier 96 and the analog output from D/A converter 98. The aforedescribed cycle is repeated until the D/A converter output reaches a sufficiently high level so that the output from comparator 97 will switch to a low state. This is sensed by the microprocessor, which then leaves the subroutine of FIG. 7 and goes on to compute the solids concentration reading as aforedescribed. If the count reaches the maximum number (255) without obtaining a low signal at the output of comparator 97, it is apparent that the amplifier output signal is not measurable and the microprocessor 86 then will enter as error routine whereby error display light 102 (FIG. 5) is illuminated and no solids concentration is computed. Error display light 102 indicates that a reading cannot be made and that the source of the problem should be checked. It may be seen that a failure of light source 54 or an opaque film over one of the windows 47 or 48 would cause an error indication at error display light 102.

As indicated hereinbefore, microprocessor 86 reads and stores the "zero" suspended solids concentration reference voltage from the amplifier as $X_o$, the high concentration reference voltage from the amplifier as $X_s$, and the amplifier value of the suspended solids concentration taken during a reading as X. The meaning of the calculations performed by the microprocessor and indicated in box 101 of FIG. 6 may be seen by reference to the graph of FIG. 8. A predetermined suspended solids concentration range of zero to 10,000 parts per million (PPM) is seen on the ordinate. The uncorrected count output from the microprocessor 86 to the D/A converter 98 is seen along the abscissa, being graduated in number of counts. The locus of desired and initially set points describing the linear relationship between suspended solids concentration and count output is seen as line 103 extending from the zero intersection to a point ($X_r$) wherein approximately 200 counts equals the full scale reading (high concentration reference level) of 10,000 PPM. The slope of line 103 equals $K_B$ which has been set in the microprocessor by the hexadecimal thumbwheel switches 28 as mentioned before. By shifting the zero reference level by $X_o$, the locus of X values shifts to the hypothetical line 105. Furthermore, by reading the actual high concentration reference point as $X_s$, the final locus of uncorrected X values becomes line 104. It can be seen that the slope of line 104 is different from that of 103 and 105 since the electronic component values have changed and the point $X_s$ is found at 240 counts rather than at 220 counts as expected due only to the zero reference level shaft. Finally, it will be noted that since the microprocessor conversion circuitry operates in accordance with curve 103, $X_c$ is converted to the proper suspended solids concentration reading $Y_c$ which is displayed in display 87. Thus, the corrective circuitry of the present invention functions to translate the X values from the line 104 (which is the actual locus of the binary count equivalent of the amplifier output values) to the line 103 where they are converted to the proper y output values for display.

It may therefore be seen that a suspended solids measuring apparatus and method have been described which include the capabilities of self-cleaning, self-calibration, and error indication, and wherein such functions are performed automatically.

Although the best mode contemplated for carrying out the present invention has been herein shown and described, it will be apparent that modification and variation may be made without departing from what is regarded to be the subject matter of the invention.

What is claimed is:

1. Apparatus for detecting the concentration of solids suspended in a solution, comprising
   a sensor head adapted to be immersed in the solution and having a chamber disposed for communication with the solution,
   means coupled to said sensor head for selectively introducing a clear liquid into said chamber,
   windows mounted in said head adjacent said chamber defining a sample path through said chamber having a predetermined sample path length therewithin,
   a light source mounted in said sensor head positioned to direct light energy along said sample path,
   a light sensor mounted in said sensor head exposed to light which has traversed said sample path and providing an output signal indicative of received light intensity,
   said means for introducing said clear liquid into said chamber being arranged to flood said sample path length with said clear liquid, whereby a low concentration of suspended solids is simulated,
   a light absorbing member disposed for motion between a position intercepting said sample path and a position remote therefrom, said light absorbing member being formed of a material arranged to absorb a predetermined portion of the light energy directed along said sample path and arranged to transmit a predetermined portion of the light energy directed along said sample path corresponding to a measurable level of suspended solids concentration when said light absorbing member is disposed in said intercepting position, whereby a high concentration of suspended solids is simulated,
   and means coupled to receive said output signal for controlling said means for introducing a clear liquid, and said light absorbing member to alternately flood and intercept said sample path, so that the output of said light sensor is calibrated by said means for controlling to provide correction for subsequent suspended solids concentration readings.

2. Apparatus as in claim 1 wherein said means for controlling includes means for activating said clear liquid introducing means and said light absorbing member at periodic intervals of time of predetermined duration.

3. Apparatus as in claim 1 wherein said means for controlling examines the output signal from the light sensor each time a concentration of suspended solids is calculated, including such calculation during the simulation of high suspended solids concentration, and provides an error indication when said signal exceeds a predetermined maximum.

4. Apparatus as in claim 1 together with means for selectively introducing a wash liquid into said chamber and forcefully directing the wash liquid against said windows whereby light absorbing matter deposited thereon is removed.

5. Apparatus as in claim 4 wherein said means for introducing a wash liquid comprises a wash liquid control valve and a wash liquid flow regulator connected to said wash liquid control valve, whereby introduction of wash liquid to said chamber is controlled at a predetermined rate.

6. Apparatus as in claim 4 wherein said means for controlling said means for introducing a clear liquid and said means for introducing a wash liquid includes means for activating each of said liquid introducing means at predetermined times and for predetermined time intervals in periodic operating cycles of predetermined duration, said means for introducing said clear liquid being activated immediately after the deactivation of said means for introducing a wash liquid.

7. Apparatus as in claim 6 wherein said means for controlling includes means for providing an error indication when said signal from said light sensor indicates a concentration of suspended solids above a predetermined range of the meter.

8. Apparatus as in claim 1 wherein said means for introducing said clear liquid comprises a flooding liquid control valve, and a flooding liquid flow regulator connected to said flooding liquid control valve, whereby introduction of said clear liquid to fill said sample path is controlled at a predetermined rate.

9. Apparatus as in claim 1 wherein said means for controlling comprises a microprocessor having a plurality of input and output ports, said means for controlling further including a digital-to-analog converter coupled to receive a succession of sequentially incremented counts from one of said output ports of said microprocessor and providing an incrementally increasing analog output in response thereto, a comparator having one input connected to said incrementally increasing output of said converter and another input coupled to receive said light sensor output signal, said comparator providing an output signal when the signal from the converter exceeds said light sensor output signal, said converter output signal being connected to an input port of said microprocessor, said microprocessor operating to arrest said count output to said converter upon reception of said comparator output signal, said microprocessor including means for converting the arrested count into an indication of the concentration of suspended solids in said chamber of said sensor head.

10. Apparatus as in claim 9 wherein the number of successive counts provided by said microprocessor is a finite number, together with means coupled to said microprocessor for indicating that the output of the apparatus is erroneous when said finite number of counts is completed without obtaining said comparator output signal.

11. Apparatus as set forth in claim 1 including a logarithmic amplifier connected to receive said light sensor output signal, said means for controlling including means for calculating connected to receive the output of said amplifier and to provide a correction thereto in accordance with shifts in the light sensor signal obtained during said low and high concentration of suspended solids simulations.

12. A device for metering the concentration of solids suspended in a solution being monitored, comprising
a sensing head having walls defining an exposed chamber for communication with the monitored solution,
windows in said walls defining a sample path through said exposed chamber of predetermined length,
a light source mounted within said sensing head and spaced from one end of said sample path in a position to direct light energy therealong,
a light sensor mounted within said sensing head and spaced from the opposite end of said sample path in a position to receive light energy which has traversed said sample path, said sensor providing an output signal related to the intensity of light energy received,
means for selectively flooding said predetermined path length with a clear liquid free of suspended solids, whereby the output signal from the sensor during such flooding provides a low suspended solids concentration reference,
means for absorbing a predetermined portion of said light energy directed along said sample path and for transmitting a predetermined portion of said light energy directed along said sample path corresponding to a measurable level of suspended solids concentration, said energy absorbing means being movable into said sample path whereby a high suspended solids concentration reference is provided by the output signal from the sensor when the energy absorbing means is in said sample path,
means for selectively moving said energy absorbing means into said sample path,
and control means for activating said means for flooding and said means for actuating said energy absorbing means in a predetermined sequence to thereby periodically provide said low and high references respectively, said control means being coupled to receive said light sensor output signals and operating to provide outputs indicative of suspended solids concentration in said solution, said control means having means for storing said low and high references and for using such references to modify said outputs indicative of suspended solids concentration in said solution.

13. A device as in claim 12 wherein said control means examines the output signal from the light sensor each time a concentration of suspended solids is calculated, including such calculation during the simulation of high reference concentration, and provides an error indication when said signal exceeds a predetermined maximum.

14. A device as in claim 12 wherein said control means comprises
a microprocessor,
converter means for receiving serially incremented binary counts from said microprocessor and providing an analog output corresponding thereto,
means for comparing said light sensor output to said converter means output and providing a signal when said converter means output is substantially equivalent to said light sensor output, said comparing means output signal being connected to said microprocessor to arrest said binary count to said converter means whereby said count in said microprocessor is indicative of suspended solids concentration in the solution.

15. A device as in claim 14 including a logarithmic amplifier for receiving said light sensor output and for providing said light sensor signal input to said comparing means.

16. A device as in claim 12 together with means for periodically removing light absorbing matter deposited on the surfaces of said windows, said means for periodically removing being actuated by said control means in said predetermined sequence immediately prior to the activation of said means for flooding.

17. A method for measuring the concentration of solids suspended in a solution within low and high limits defining a predetermined concentration range, comprising the steps of
defining a predetermined path length through the solution,
directing a light beam along the path,
sensing the intensity of the light beam after traversing the path and providing an output indicative thereof,
flooding the predetermined path length periodically with a clear liquid substantially free of suspended solids,
storing the light beam intensity output during the step of flooding as a low concentration reference,
absorbing a predetermined portion of the light beam intensity periodically while simultaneously transmitting another predetermined portion of the light beam intensity with the latter portion corresponding to a high and measurable suspended solids concentration reference,
storing the light beam intensity output during the step of absorbing and transmitting as a high concentration reference,
and correcting subsequent suspended solids concentration measurements in accordance with the low concentration reference and the high concentration reference so that the subsequent measurements will be upon a predetermined scale within the predetermined concentration range.

18. A method as in claim 17 together with the step of periodically flushing the structure defining the predetermined path length to remove light attenuating matter therefrom, said flushing step being undertaken immediately prior to said flooding step.

19. A method as in claim 17 wherein the step of correcting is performed only within a finite range of light beam intensity outputs, together with the step of examining the light beam intensity output at all times, including during the period when a high concentration of suspended solids is being simulated, and with the step of indicating that the suspended solids concentration measurement is in error when the light beam intensity output exceeds the finite range.

* * * * *